United States Patent

Kawakishi et al.

[11] Patent Number: 5,606,035
[45] Date of Patent: Feb. 25, 1997

[54] SESAMINOL GLUCOSIDES

[76] Inventors: Shunrou Kawakishi, 70 Aza-Yawata, Oaza-Miyoshi, Miyoshi-cho, Nishikamo-gun, Aichi, Japan; Toshihiko Osawa, 7-9-8 Osizawadai, Kasugai, Aichi, Japan

[21] Appl. No.: 273,252

[22] Filed: Jul. 11, 1994

[30] Foreign Application Priority Data

Jan. 25, 1994 [JP] Japan ................................. 6-023828

[51] Int. Cl.$^6$ ............................. C07H 3/02; C07H 3/04
[52] U.S. Cl. ..................... 536/4.1; 536/123.1; 536/124; 536/128; 424/195.1; 435/72; 435/74; 549/435
[58] Field of Search ..................... 435/72, 74; 536/4.1, 536/124, 123.1, 128; 549/435; 424/195.1

[56] References Cited

U.S. PATENT DOCUMENTS

| | | | |
|---|---|---|---|
| 4,649,206 | 3/1987 | Namiki et al. | 549/435 |
| 4,708,820 | 11/1987 | Namiki et al. | 549/435 |
| 5,336,496 | 8/1994 | Akimoto et al. | 424/195.1 |

*Primary Examiner*—James O. Wilson

[57] ABSTRACT

New sesaminol glucosides, which are glucosides of lignan compounds of a specified structure, are effective in preventing oxidation of lipids in an aqueous solvent. Such sesaminol glucosides are produced substantially in pure form by obtaining an aqueous extract from crushed and defatted sesame seeds, processing the extract with β-glucosidase to obtain a processed sesame product which is itself an effective anti-oxidant, and make separations by liquid chromatography under specified conditions.

1 Claim, No Drawings

SESAMINOL GLUCOSIDES

BACKGROUND OF THE INVENTION

It is being pointed out that, when lipids in food are oxidized, not only is the flavor of the food spoiled, but the products of such oxidation also cause cancer. It is therefore an object of this invention to provide sesaminol glucosides capable of generating sesaminol by hydrolysis during the processing of meats such as hams and sausages and thereby effectively inhibiting the oxidation of lipids in such meats, as well as processed sesame products containing them and methods of producing them.

Natural anti-oxidants such as sesaminol, sesamolinol and pinoresinol have been known (Japanese Patent Publication Tokkai 62-581, U.S. Pat. Nos. 4,649,206 and 4,708,820). They are lignan compounds contained in sesame seeds and since they are natural, they have the advantage of being reasonably safe. Their usefulness is limited, however, because all these natural anti-oxidants are oil-soluble but not water-soluble.

It has also been known that, if a water-soluble medium is used for extraction of sesame seeds, glucosides of such lignan compounds appear in the extract (Japanese Patent Publications Tokko 61-26342 and Tokkai 62-238287). The glucosides appearing in such extracts are water-soluble, and hence such extracts can be used as a water-soluble anti-oxidant. The structure of such glucosides, however, is unknown. Thus, even if such an extract or a product obtained by condensing or physically refining it is used as a water-soluble anti-oxidant, the effect is not sufficiently high.

SUMMARY OF THE INVENTION

One of the problems to be solved by this invention, therefore, is that the use of known natural anti-oxidants is limited because they are oil-soluble but not water-soluble. Another problem is that known extracts of sesame seeds obtained by the use of a water-soluble solvent are not sufficiently effective as a water-soluble anti-oxidant.

As a result of diligent research in view of the problems described above, the present inventors have discovered that a new kind of sesaminol glucoside can be obtained if sesame seeds are processed in a specified manner, that such new sesaminol glucosides generate sesaminol by hydrolysis and the sesaminol thus generated can inhibit oxidation of lipids effectively.

DETAILED DESCRIPTION OF THE INVENTION

The present invention relates to sesaminol glucosides shown by Formula (1) given below substantially in pure form:

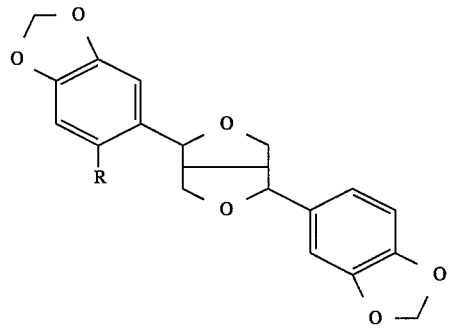

Formula (1)

where -R is an organic group shown by Formula (2) or (3) given below:

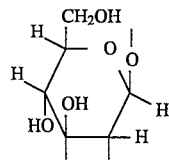

Formula (2)

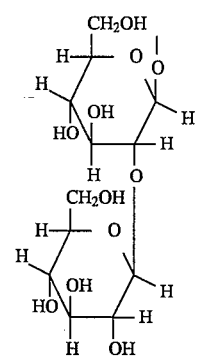

Formula (3)

Sesaminol glucosides according to the present invention can be obtained by a process comprising the following three steps: (1) the first step of crushing and defatting sesame seeds and thereafter obtaining an extract by extracting them with water, an aqueous solvent or a mixed solvent thereof; (2) the second step of processing this extract with β-glucosidase and thereby obtaining a processed sesame product containing sesaminol glucosides; and (3) the third step of carrying out liquid chromatography by using water, an aqueous solvent or a mixed solvent thereof as mobile phase, for separating sections containing sesaminol glucosides to thereby obtain a sesaminol glucoside substantially in pure form.

Examples of sesame seeds serving as the base material in the aforementioned first step include not only sesamum indicum which is a cultivated species, but also many wild species.

From the point of view of extraction efficiency, however, crushed seeds are preferred. Since sesame seeds contain about 50% of oil, furthermore, it is desirable from the point of view of extraction efficiency to have their oil component removed. According to the present invention, therefore, sesame seeds are extracted after they are crushed and defatted. As an example of crushed and defatted sesame seeds, use may be made of those obtained by first crushing sesame seeds by a mill and then defatted by using hexane. Use may also be made of defatted sesame seeds after oil has been extracted by means of an expeller in an ordinary production process of edible sesame seed oil.

Such crushed and defatted sesame seeds are extracted with water, an aqueous solvent or a mixed solvent thereof. Examples of aqueous solvent that may be used include lower alcohols such as methanol, ethanol, n-propyl alcohol and isopropyl alcohol, as well as acetone, dimethyl acetamide, and dimethyl formamide, but water, lower alcohols and mixtures of water and lower alcohol are preferred. Particularly preferable are mixed solvents of water and ethanol.

In the extraction process, it is preferred to use 2–7 times in weight of solvent with respect to crushed and defatted sesame seeds. If it is less than twice in weight, the solvent is absorbed by the crushed and defatted sesame seeds and the extraction process becomes difficult to perform. If it is over seven times in weight, on the other hand, the extraction efficiency is adversely affected. Although the extraction operation can be carried out at any temperature, it is preferable to keep the temperature within the range of 0°–50° C. in order to prevent deterioration of the target substance. According to a preferred extraction process, 3–5 times as much solvent in weight is used at room temperature with stirring for 8–24 hours and followed by a process of filtering.

An extract liquid thus obtained may be used directly as the extract in the aforementioned second step, depending on the kind of solvent used for the extraction, but it is preferred to condense it at a temperature within the range of 0°–50° C. and to further freeze-dry it so that the target substance will not be deteriorated. In other words, the condensed liquid or the freeze-dried material obtained therefrom by freeze-drying is used as the extract in the second step.

In the second step, the extract thus prepared in the first step is processed by adding β-glucosidase in an aqueous system. A processed sesame product containing sesaminol glucosides according to the present invention by 0.03–0.3 weight % is obtained by this process. The sesaminol glucosides according to this invention contained in this processed sesame product are already of such structure so as not to undergo hydrolysis in the presence of β-glucosidase. In other words, these sesaminol glucosides are different from the glucosides found in the extract obtained in the first step, or glucosides of unknown structure with a β-glucoside linkage between a group shown by Formula (2) or (3) and other saccharides.

This invention does not impose any particular limitation on the method of processing with β-glucosidase, but it may be carried out, for example, by adjusting the extract obtained in the first step in an aqueous system with pH=3–7, adding β-glucosidase thereto and stirring for a specified length of time at 50° C.

In the aforementioned third step, the processed sesame product obtained in the second step is subjected to liquid chromatography with water, an aqueous solvent or a mixed solvent thereof used as its mobile phase for separating sections containing sesaminol glucosides to thereby obtain a sesaminol glucoside substantially in pure form.

Well known separation methods by liquid chromatography can be used. Known kinds of stationary phase, for example, of silica gel, alumina, ODS silica, cross-linked polystyrene and ion exchange resins may be appropriately selected for use. Examples of mobile phase include water, aqueous solvents and their mixtures. The separation process may be carried out by using a single stationary phase or by repeating with different kinds of stationary phases.

Sesaminol glucosides according to the present invention thus separated has been analyzed, as will be described in detail below, and it was determined by such analyses that they are of a chemical structure shown by Formula (1) given above. In other words, they may be sesaminol 2'-O-β-D-glucopyranoside represented by Formula (1) where R is an organic group shown by Formula (2), or sesaminol 2'-O-β-D-glucopyranosyl(1→2)-β-D-glucopyranoside represented by Formula (1) where R is an organic group shown by Formula (3).

The sesaminol glucosides according to the present invention and the processed sesame products containing them are water-soluble substances and effective for preventing oxidation of lipids in aqueous solvents.

In a system containing both lipids and an aqueous solvent, prevention of oxidation of the lipids by using a sesaminol glucoside according to the present invention or a processed sesame product containing it can be accomplished by causing the sesaminol glucoside or the processed sesame product to be both contained in the aqueous solvent. In this situation, the oxidation of lipids can be even more efficiently accomplished if the system containing the lipids and the aqueous solvent also contain enzymes for the growth of thalli such as rice koji, soybean koji and bacillus subtilis, or those in biotissues capable of causing hydrolysis of glucopyranoside linkage.

Examples of such system containing both lipids and an aqueous solvent include systems like cow milk and soybean milk wherein the lipids are emulsified and dispersed in the aqueous solvent, meat tissue systems like fish meat, pork and beef and processed meats such as hams and sausages wherein the lipids and the aqueous solvent coexist, and many kinds of biotissues wherein water and lipids coexist.

The present invention does not impose any specific limitation on the amount of the sesaminol glucosides according to the invention, or processed sesame products containing them, to be caused to be contained in a system containing both water and lipids. Generally, however, use is made at a rate of about 1–200 μM of the sesaminol glucoside of the invention per gram of the lipids.

Neither does the present invention impose any specific limitation on the method of causing the sesaminol glucosides according to the present invention, or processed sesame products containing them, to be caused to be contained in a system wherein water and lipids coexist. For processed foods such as processed meats, yogurt and soybean milk, they may be added directly during the process of mixing the base materials. In the case of biotissues, oral administration is also possible.

Experimental Examples

Sesame seeds from China 250 g were crushed and put in a flask. After one liter of hexane was added and stirred for 5 hours at room temperature, it was filtered. This operation was repeated twice more and the solid component was dried by wind at room temperature to obtain 115 g of defatted sesame seeds. They were then transferred into a flask and after ethanol 736 g and water 184 g were added and stirred together for 15 hours at room temperature, it was filtered to obtain 355 g of a filtrate. This filtrate was condensed to 80 g at temperature below 40° C. under a reduced pressure condition and 2.7 g of extract (Fraction R-1) was obtained by freeze-drying.

Separately, an extract 6 g was similarly obtained. After 50 ml of chloroform and 50 ml of water were added to this extract and the mixture was shaken vigorously and left quietly, the chloroform layer was separated and chloroform was distilled away to obtain 1.8 g of chloroform-soluble component. After acetone 30 ml was added to this chloroform-soluble component and the mixture was stirred, the acetone-insoluble component which was separated by filtering was dried in a desiccator to obtain 0.8 g thereof. This acetone-insoluble component was dissolved in 10 ml of a mixed solution of chloroform/acetone=4/1 and introduced from the top into a glass column filled with silica gel (Wakogel C-100, tradename of Wako Pure Chemical Industries, Ltd.) for adsorption on the silica gel. A mixed solvent of acetone/methanol=9/2 (50 ml) was caused to flow as mobile phase to collect the eluting liquid. The solvent was removed therefrom and 70 mg of condensed glucoside (Fraction R-2) was obtained.

Separately, 2.7 g of extract was similarly obtained. It was dissolved in 100 g of water with pH adjusted to 5.0 and 100 mg of β-glucosidase was added for a processing for 20 hours at 40° C. Next, this processed liquid was transferred into a separating funnel with capacity of 500 ml, and 200 ml of ethyl acetate was added for extraction. The ethyl acetate extract was condensed to 60 g at temperature below 40° C. under a reduced pressure condition and further freeze-dried to obtain 1.5 g of a processed sesame product (Fraction C).

Still further separately, 2.7 g of extract was obtained and 1.5 g of processed sesame product was obtained therefrom. This processed sesame product was further separated by liquid chromatography under the following conditions:

Stationary phase: Develosil ODS-10 (tradename of product by Nomura Chemical Co., Ltd.)

Column diameter: 20 mm

Column length: 250 mm

Mobile phase: Methanol/water=60/40 (v/v)

Mobile phase flow rate: 6 ml/min.

Detection: UV 280 nm

After the section flowing out at retention time of 19 minutes was collected, it was condensed at temperature below 40° C. under a reduced pressure condition, and 113.8 mg of a solid material (Fraction A) was obtained by freeze-drying. Another section flowing out at retention time of 15 minutes was collected, condensed at temperature below 40° C. under a reduced pressure condition and freeze-dried to obtain 8.9 mg of another solid material (Fraction B).

On the basis of the various analyses described below, it was determined that Fraction A, obtained by such extraction process, processing with β-glucosidase and separation by liquid chromatography, is sesaminol 2'-O-β-D-glucopyranoside represented by Formula (1) with R being an organic group shown by Formula (2) and that Fraction B is sesaminol 2'-O-β-D-glucopyranosyl(1→2)-β-D-glucopyranoside represented by Formula (1) with R being an organic group shown by Formula (3):

Analysis of Fraction A

Mass spectrum:

[M+1]+; 533,

[M+Na]+; 555

Ultraviolet spectrum:

$\lambda_{max}$: 290.2 nm, 236.4 nm $\epsilon_{max}$: 8710, 10000

Specific rotation $[\alpha]_D$: −6.2

$^1$HNMR δ chemical shift (assigned hydrogen): 2.98 (2H, m), 3.50 (4H, m), 3.72 (1H, m), 3.87 (1H, dd), 3.94 (1H,m), 4.06 (1H, d), 4.19 (1H, d), 4.26 (1H, d), 4.63 (1H, d), 4.85 (1H, d), 5.18 (1H, d), 5.93 (2H, s), 5.96 (2H, s), 6.78 (1H, d), 6.81 (1H, dd), 6.82 (2H, s), 6.85 (1H, d)

$^{13}$CNMR δ chemical shift (assigned carbon): 54.7 (C-5), 55.4 (C-1), 62.6 (G-6), 71.2 (G-4), 71.9 (C-4), 73.6 (C-8), 74.7 (G-2), 77.8 (G-3), 78.0 (G-5), 82.1 (C-2), 85.9 (C-6), 99.6 (C-3'), 101.9 (-OC"H$_2$-O-), 102,0 (-OC"H$_2$-O-), 103.4 (G-1), 105.8 (C-6'), 107.2 (C-2"), 108.6 (C-5"), 120.1 (C-6"), 125.5 (C-1'), 136.8 (C-1"), 143.3 (C-4'), 147.1 (C-5'), 147.8 (C-3"), 148.7 (C-4"), 150.4 (C-2')

Analysis of Fraction B

Mass spectrum:

[M+1]+; 695,

[M+Na]+; 717

Ultraviolet spectrum:

$\lambda_{max}$: 290.6 nm, 235.8 nm $\epsilon_{max}$: 9120, 10233

Specific rotation $[\alpha]_D$: −25.6

$^1$HNMR δ chemical shift (assigned hydrogen): 2.81 (1H, m), 2.89 (1H, m), 3.03 (1H), 3.10 (1H), 3.19 (1H), 3.20 (1H), 3.21 (1H), 3.40 (1H), 3.41 (1H), 3.53 (1H), 3.54 (1H), 3.55 (1H), 3.56 (1H), 3.70 (1H), 3.78 (1H, dd), 4.00 (1H, dd), 4.18 (2H, dd), 4.59 (1H, d), 4.63 (1H, d), 4.96 (1H, d), 5.06 (1H, d), 5.95 (2H, d), 5.99 (2H, s), 6.80 (1H, s), 6.12 (1H, s), 6.83 (1H, dd), 6.84 (1H, d), 6.91 (1H, d)

$^{13}$CNMR δ chemical shift (assigned carbon): 53.9 (C-5), 54.2 (C-1), 60.3 (G-6'), 60.6 (G-6), 69.3 (G-4'), 69.5 (G-4), 71.0 (C-4), 72.3 (C-8), 74.9 (G-2'), 76.3 (G-5'), 76.6 (G-5), 76.8 (G-3), 77.0 (G-3'), 80.5 (C-2), 81.4 (G-2), 84.4 (C-6), 97.5 (C-3'), 98.7 (G-1), 100.9 (-OCH$_2$-O-), 101,0 (-OCH$_2$-O-), 104.0 (G-1'), 104.6 (C-6'), 107.9 (C-2"), 119.3 (C-5"), 124.0 (C-6"), 135.5 (C-1'), 141.5 (C-1"), 146.3 (C-5'), 146.5 (C-4"), 147.3 (C-3"), 148.1 (C-2')

Evaluation of anti-oxidation property

Soybean milk 500 ml and Fraction A 70 μM were placed inside a one-liter beaker for a processing for three hours with temperature kept at 40° C. with the bubbling of air. Similarly, other soybean milk samples (fraction-added samples) were prepared with 70 μM of Fraction B added, 40 mg of Fraction C added, 40 mg of Fraction R-1 added, 40 mg of Fraction R-2 added and 70 μM of sesaminol added, as well as a sample with nothing added (comparison sample). Each soybean milk sample 0.1 ml after the processing and aqueous solution of t-butyl hydroperoxide (2.16 mg/ml) 0.05 ml were placed inside a test tube with a screw cap and, after it was shaken for 20 minutes at 37° C., 20% aqueous solution of trichloroacetic acid 1 ml and 0.67% aqueous solution of 2-thiobarbituric acid 2 ml were added, it was heated for 10 minutes at 100° C. for color development, centrifugal separation was carried out for 15 minutes at 3500 rpm, the light absorptivity of the supernatant liquid was measured at 532 nm, and the coloring degree was calculated by Formula (4) given below:

(Coloring degree)=100×(Absorptivity of supernatant liquid of fraction-added sample)/(Absorptivity of supernatant liquid of comparison sample).    Formula (4)

The results of the experiment are shown in Table 1.

The coloring of the supernatant liquid depends on the generation of lipids peroxides such that low coloring degrees mean high efficiency in preventing the oxidation of lipids. In the above experiment, sesaminol which is an oil-soluble natural anti-oxidant was used for the purpose of comparison as an example which does not easily mix with lipids in an aqueous solvent.

Table 1 clearly indicates that sesaminol glucosides according to the present invention and processed sesame products containing them are effective in preventing the oxidation of lipids in an aqueous solvent.

TABLE 1

| Samples | Coloring Degree |
| --- | --- |
| Sample with Fraction A added | 22 |
| Sample with Fraction B added | 24 |
| Sample with Fraction C added | 39 |
| Sample with Fraction R-1 added | 87 |
| Sample with Fraction R-2 added | 52 |
| Sample with sesaminol added | 63 |
| Comparison sample | 100 |

What is claimed is:

1. A sesaminol glucoside given by Formula (1) given below substantially in pure form:

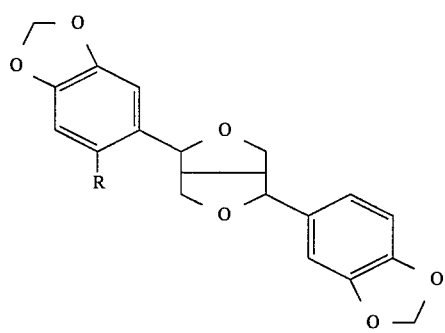
Formula (1)
where -R is an organic group given by Formula (2) or (3) given below:
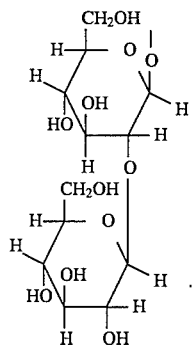
Formula (2)
Formula (3)
\* \* \* \* \*

UNITED STATES PATENT AND TRADEMARK OFFICE
CERTIFICATE OF CORRECTION

PATENT NO. : 5,606,035
DATED : February 25, 1997
INVENTOR(S) : Shunrou Kawakishi et al.

It is certified that error appears in the above-indentified patent and that said Letters Patent is hereby corrected as shown below:

Please add to the Title Page:

[73] Assignee: Takemoto Yushi Kabushiki Kaisha, Japan

Signed and Sealed this

Eighth Day of July, 1997

Attest:

BRUCE LEHMAN

Attesting Officer

Commissioner of Patents and Trademarks